US010749181B2

(12) United States Patent
Wang et al.

(10) Patent No.: US 10,749,181 B2
(45) Date of Patent: Aug. 18, 2020

(54) OLIGOMER AND LITHIUM BATTERY

(71) Applicant: National Taiwan University of Science and Technology, Taipei (TW)

(72) Inventors: Fu-Ming Wang, Taipei (TW); Chorng-Shyan Chern, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 406 days.

(21) Appl. No.: 15/406,398

(22) Filed: Jan. 13, 2017

(65) Prior Publication Data

US 2018/0145375 A1    May 24, 2018

(30) Foreign Application Priority Data

Nov. 23, 2016 (TW) .............................. 105138359 A

(51) Int. Cl.
*H01M 4/62* (2006.01)
*H01M 10/42* (2006.01)
*H01M 10/0567* (2010.01)
*H01M 10/0525* (2010.01)
*C07D 239/62* (2006.01)
*C09D 4/00* (2006.01)

(52) U.S. Cl.
CPC ......... *H01M 4/62* (2013.01); *H01M 10/0525* (2013.01); *H01M 10/0567* (2013.01); *H01M 10/4235* (2013.01); *C07D 239/62* (2013.01); *C09D 4/00* (2013.01)

(58) Field of Classification Search
CPC ......... H01M 10/4235; H01M 10/0567; H01M 10/052; H01M 10/0525; H01M 4/64; C07D 239/62; C09D 4/00
See application file for complete search history.

(56) References Cited

U.S. PATENT DOCUMENTS

| 7,560,194 B2 | 7/2009 | Lin et al. | |
|---|---|---|---|
| 2007/0202403 A1* | 8/2007 | Oh | H01M 4/133 429/217 |
| 2014/0017547 A1* | 1/2014 | Eichinger | H01M 10/052 429/144 |
| 2014/0037924 A1* | 2/2014 | Furuta | C09J 7/22 428/214 |
| 2014/0175337 A1* | 6/2014 | Chern | C07D 207/452 252/506 |

(Continued)

FOREIGN PATENT DOCUMENTS

| TW | I453971 | 9/2014 |
|---|---|---|
| TW | 201521265 | 6/2015 |
| TW | I494350 | 8/2015 |

(Continued)

OTHER PUBLICATIONS

Machine Translation of WO-2011089947-A1 (published Jul. 2011).*

(Continued)

*Primary Examiner* — Eugenia Wang
(74) *Attorney, Agent, or Firm* — J.C. Patents

(57) ABSTRACT

An oligomer and a lithium battery are provided. The oligomer is obtained by a reaction of epoxy acrylate and barbituric acid. The lithium battery includes an anode, a cathode, a separator, an electrolyte solution and a packaging structure, wherein the cathode includes the oligomer.

10 Claims, 2 Drawing Sheets

(56) References Cited

U.S. PATENT DOCUMENTS

2015/0185368 A1* 7/2015 Nagase .................... G02B 1/14
349/96

FOREIGN PATENT DOCUMENTS

TW           201619207       6/2016
WO    WO-2011089947 A1 *  7/2011  ........... C08G 59/308

OTHER PUBLICATIONS

Nadya, "The investigations of coupling agent effects on self terminated of branch architecture (STOBA) in lithium ion battery," Master's thesis, Jul. 2016, Chemical Engineering Department, National Taiwan University of Science and Technology.
"Office Action of Taiwan Counterpart Application," dated Feb. 9, 2017, p. 1-p. 5, in which the listed reference was citied.

* cited by examiner

OLIGOMER AND LITHIUM BATTERY

CROSS-REFERENCE TO RELATED APPLICATION

This application claims the priority benefit of Taiwan application serial no. 105138359, filed on Nov. 23, 2016. The entirety of the above-mentioned patent application is hereby incorporated by reference herein and made a part of this specification.

BACKGROUND OF THE INVENTION

1. Field of the Invention

The invention is related to an oligomer and a battery, and particularly related to an oligomer for a lithium battery and a lithium battery.

2. Description of Related Art

Because the primary battery doesn't meet the environmental protection demands, therefore, the market demand of the rechargeable and discharge-repeatable secondary lithium battery having characteristics such as light weight, high voltage and high energy density gradually increases in recent years. Therefore, the demand about the performance of the secondary lithium battery such as lightweight, durability, high voltage, high energy density and high safety is getting higher and higher. Especially, the application and expansion potential of the secondary lithium battery on the light electric vehicles, electric vehicles, and large-scale electricity storage industry is considerably high.

However, among the commercialized secondary lithium battery on the general market, because when the lithium transition metal oxide is used as the cathode in the high temperature application, the cathode easily reacts with the electrolytes and is damaged thereby. So, the oxygen in the lithium metal oxide is released to participate in the combustion reaction. This is one of the main reasons leading to the explosion, expansion and performance degradation of the secondary lithium battery. Therefore, how to make the cathode material continue to maintain structural stability in high temperature applications is one of the desired goals of those skilled in the art currently.

SUMMARY OF THE INVENTION

The invention provides an oligomer, able to be applied in the cathode material of the lithium battery, so that the lithium battery has excellent performance and safety.

The invention provides a lithium battery, having the above-mentioned oligomer.

The oligomer of the invention is obtained by a reaction of epoxy acrylate (EA) resin and barbituric acid (BTA).

In an embodiment of the oligomer of the invention, the molar ratio of the epoxy acrylate resin to the barbituric acid is between 1:1 and 4:1, for example.

In an embodiment of the oligomer of the invention, the epoxy acrylate resin has at least one acrylic acid group.

In an embodiment of the oligomer of the invention, the epoxy acrylate resin has a structure represented by formula 1:

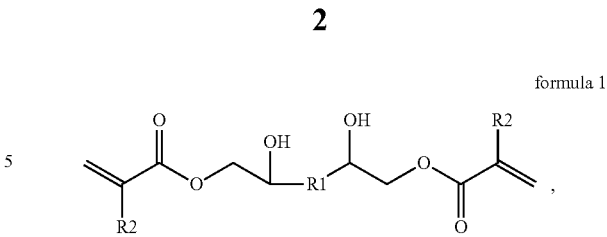

formula 1 wherein R1 is substituted or unsubstituted C1-C10 alkyl, substituted or unsubstituted C6-C10 aryl or halogen atom; R2 is —H, —CH$_3$ or —CF$_3$.

In an embodiment of the oligomer of the invention, the epoxy acrylate resin has a structure represented by formula 2:

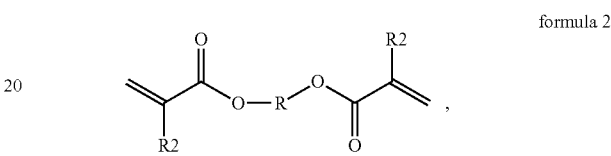

formula 2 wherein R is substituted or unsubstituted C1-C10 alkyl or ether group; R2 is —H, —CH$_3$ or —CF$_3$.

In an embodiment of the oligomer of the invention, R is C1-C10 alkyl substituted by acrylic acid group.

In an embodiment of the oligomer of the invention, the barbituric acid has a structure represented by formula 3:

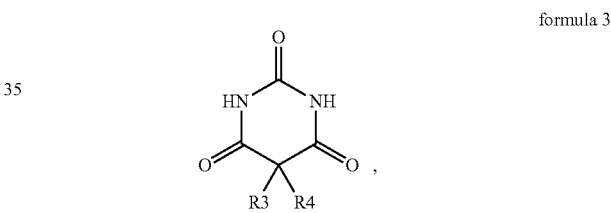

formula 3 wherein R3 and R4 are each independently —H, —CH$_3$, —C$_2$H$_5$, —C$_6$H$_5$, —CH(CH$_3$)$_2$, —CH$_2$CH(CH$_3$)$_2$, —CH$_2$CH$_2$CH(CH$_3$)$_2$ or

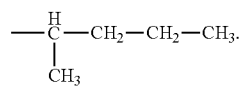

The lithium battery of the invention includes an anode, a cathode, a separator, an electrolyte solution and a packaging structure. The cathode is separately disposed from the anode, and the cathode includes the above-mentioned oligomer. The separator is disposed between the anode and the cathode, and the separator, the anode and the cathode define an accommodation area. The electrolyte solution is disposed in the accommodation area. The packaging structure covers the anode, the cathode and the electrolyte solution.

In an embodiment of the lithium battery of the invention, the electrolyte solution includes an organic solvent, lithium salt and an additive.

In an embodiment of the lithium battery of the invention, the additive is monomaleimide, polymaleimide, bismaleimide, poly-bismaleimide, copolymer of bismaleimide and monomaleimide, vinylene carbonate or a mixture thereof, for example.

Based on the above, through the preparation by the usage of epoxy acrylate resin and barbituric acid, the oligomer of the invention can be applied in the cathode material of the lithium battery, so that the lithium battery can have excellent battery efficiency and charge-discharge cycle life, and have higher safety.

To make the above features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
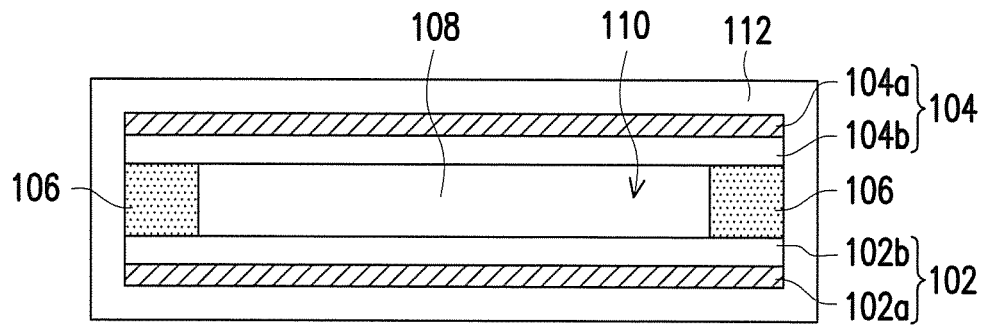
FIG. 1 is a schematic cross-sectional diagram of the lithium battery according to the embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

To prepare the oligomer able to be applied in the cathode material lithium battery so that the lithium battery has excellent performance and safety, epoxy acrylate resin and barbituric acid are used in the invention to perform a reaction to prepare the oligomer. Embodiments are described in the following paragraphs as a description to prove that the invention can actually be realized.

In the embodiment of the invention, epoxy acrylate resin reacts with barbituric acid to prepare the oligomer.

<Epoxy Acrylate Resin>

In the invention, the epoxy acrylate resin has at least one acrylic acid group. That is, in the embodiment of the invention, the epoxy acrylate resin can have an acrylic acid group at a single side or can have acrylic acid groups at both sides, or can have at least one acrylic acid group in the backbone structure as substituent group.

In an embodiment of epoxy acrylate resin, epoxy acrylate resin can have a structure represented by formula 1:

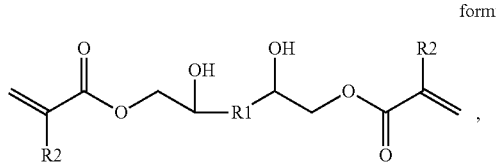

formula 1 wherein R1 is substituted or unsubstituted C1-C10 alkyl, substituted or unsubstituted C6-C10 aryl or a halogen atom. R2 is —H, —CH$_3$ or —CF$_3$. Under the condition of the substituent in R1 not being an acrylic acid group, the above-mentioned epoxy acrylate resin has two acrylic acid groups (located at two ends of epoxy acrylate resin separately). Of course, in other embodiments, epoxy acrylate resin can also have one acrylic acid group in only one of the ends. Or, the substituent in R1 can also be an acrylic acid group.

In another embodiment of epoxy acrylate resin, epoxy acrylate resin can have a structure represented by formula 2:

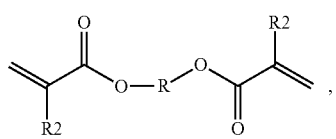

formula 2 wherein R is substituted or unsubstituted C1-C10 alkyl or an ether group. R2 is —H, —CH$_3$ or —CF$_3$. For example, epoxy acrylate resin can have the following structure:

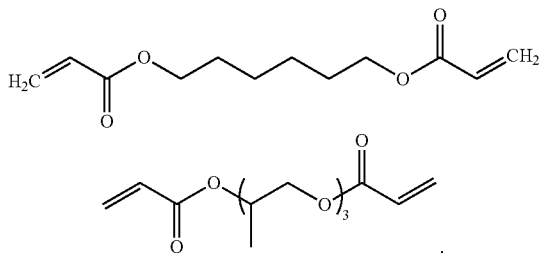

Under the condition of the substituent in R not being an acrylic acid group, the above-mentioned epoxy acrylate resin has two acrylic acid groups (located at two ends of epoxy acrylate resin separately). Of course, in other embodiments, epoxy acrylate resin can also have one acrylic acid group in only one of the ends. Or, in other embodiments, R can be C1-C10 alkyl substituted by at least one acrylic acid group. For example, epoxy acrylate resin can have the following structure:

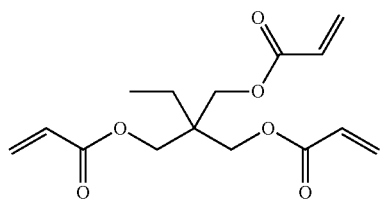

At this time, the above-mentioned epoxy acrylate resin has three acrylic acid groups. That is, R is alkyl substituted by one acrylic acid group, and two acrylic acid groups locate on two ends of epoxy acrylate resin separately. Of course, in another embodiment, epoxy acrylate resin having similar structure can also have 4 acrylic acid groups. That is, R is alkyl substituted by two acrylic acid groups.

<Barbituric Acid>
barbituric acid has a structure represented by formula 3:

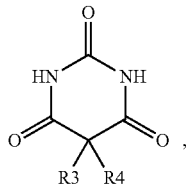

formula 3 wherein R3 and R4 are each independently —H, —CH$_3$, —C$_2$H$_5$, —C$_6$H$_5$, —CH(CH$_3$)$_2$, —CH$_2$CH(CH$_3$)$_2$, —CH$_2$CH$_2$CH(CH$_3$)$_2$ or

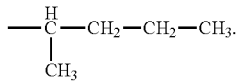

In the embodiment of the invention, the oligomer is obtained through a reaction of epoxy acrylate resin and barbituric acid. Furthermore, Michael addition reaction is used to make epoxy acrylate resin and barbituric acid dissolved in solvent to perform the addition polymerization, so as to prepare the oligomer of the invention. A molar ratio of the epoxy acrylate resin to the barbituric acid in use is between 1:1 and 4:1, for example, according to the type of the epoxy acrylate resin in use, that is, according to the number of the acrylic acid group in the epoxy acrylate resin in use. If the molar ratio of the epoxy acrylate resin to the barbituric acid is lower than 1:1, the reactivity will be poor. If the molar ratio of the epoxy acrylate resin to the barbituric acid is higher than 4:1, the electrochemical side reaction will easily occur. The temperature of the above-mentioned addition polymerization reaction is between 50° C. and 200° C., for example, the reaction time is between 0.25 hour and 5 hours, for example. The above-mentioned solvent can be organic solvent, such as (but not limited thereto) N-methyl pyrollidone (NMP), γ-butylrolactone (GBL) or propylene carbonate (PC). The above-mentioned solvent can be used singly or in a mixture.

The oligomer of the invention can be applied in the cathode material of the lithium battery. Specifically, the oligomer of the invention has excellent heat reactivity, so a protection layer is formed on the surface of the cathode material, to effectively prevent the structure of the cathode from being damaged by high environment temperature. The reason is as follows: Because the formed oligomer has highly branched structure, stable organic polymer can be formed by a reaction of the formed oligomer and the metal oxide in the general cathode material, and because the oligomer has high thermal reactivity, high thermal stability and rigid chemical structure, therefore, the formed protection layer can have high thermal stability. In such a way, under high environment temperature, the lithium battery having the cathode material including the oligomer of the invention can have excellent capacity, battery efficiency and safety, and have excellent battery cycle life.

In the following paragraphs, the lithium battery including the oligomer of the invention is described.

FIG. 1 is a schematic cross-sectional diagram of the lithium battery according to the embodiment of the present invention. Please refer to FIG. 1, the lithium battery 100 includes an anode 102, a cathode 104, a separator 106, an electrolyte solution 108 and a packaging structure 112.

The anode 102 includes an anode metal foil 102a and an anode material 102b, wherein the anode material 102b is disposed on the anode metal foil 102a through coating or sputtering. The anode metal foil 102a is a copper foil, an aluminum foil, a nickel foil or a highly conductive stainless steel foil, for example. The anode material 102b is carbides or lithium metal, for example. The carbides are, for example, carbon powders, graphite, carbon fibers, carbon nanotubes, graphene or mixtures thereof. However, in other embodiments, the anode 102 can only include the anode material 102b.

The cathode 104 and the anode 102 are separately disposed. The cathode 104 includes a cathode metal foil 104a and a cathode material 104b, wherein the cathode material 104b is disposed on the cathode metal foil 104a through coating. The cathode metal foil 104a is a copper foil, an aluminum foil, a nickel foil or a highly conductive stainless steel foil, for example. The cathode material 104b includes the oligomer of the invention and lithium mixed transition metal oxide. Lithium mixed transition metal oxide is, for example, LiMnO$_2$, LiMn$_2$O$_4$, LiCOO$_2$, Li$_2$Cr$_2$O$_7$, Li$_2$CrO$_4$, LiNiO$_2$, LiFeO$_2$, LiNi$_x$Co$_{1-x}$O$_2$, LiFePO$_4$, LiMn$_{0.5}$Ni$_{0.5}$O$_2$, LiMn$_{1/3}$Co$_{1/3}$Ni$_{1/3}$O$_2$, LiMc$_{0.5}$Mn$_{1.5}$O$_4$ or a combination thereof, wherein 0<x<1, Mc is divalent metal.

Based on an amount of the cathode material 104b being 100 parts by weight, an amount of the oligomer is 0.5 parts by weight to 5 parts by weight (preferably 1 part by weight to 3 parts by weight), the amount of lithium mixed transition metal oxide is 80 parts by weight to 95 parts by weight, for example. If the content of the oligomer is lower than 0.5 parts by weight, the battery safety characteristic is not obvious; if the content of the oligomer is higher than 5 parts by weight, the battery cycle life is poor.

In addition, the lithium battery 100 can further include a polymer binder. The polymer binder reacts with the anode 102 and/or cathode 104, to increase the mechanical properties of the electrodes. Specifically, the anode material 102b can be adhered on the anode metal foil 102a through the polymer binder, and the cathode material 104b can be adhered on the cathode metal foil 104a through the polymer binder. The polymer binder is, for example, polyvinylidene difluoride (PVDF), styrene butadiene rubber (SBR), polyamide, melamine resin or a combination thereof.

The separator 106 is disposed between the anode 102 and the cathode 104, and the separator 106, the anode 102 and the cathode 104 define the accommodation area 110. The material of the separator 106 is insulation material, such as polyethylene (PE), polypropylene (PP), or a composite structure formed by the above-mentioned materials (PE/PP/PE, for example).

The electrolyte solution 108 is disposed in the accommodation area 110. The electrolyte solution 108 includes an organic solvent, lithium salt and an additive. The amount of the organic solvent is 55 wt % to 90 wt % of the electrolyte solution 108, the amount of the lithium salt is 10 wt % to 35 wt % of the electrolyte solution 108, the amount of the additive is 0.05 wt % to 10 wt % of the electrolyte solution 108. However, in other embodiments, the electrolyte solution 108 can also contain no additive.

The organic solvent is, for example, γ-butyrolactone, ethylene carbonate (EC), propylene carbonate, diethyl carbonate (DEC), propyl acetate (PA), dimethyl carbonate (DMC), ethylmethyl carbonate (EMC) or a combination thereof.

Lithium salt is, for example, $LiPF_6$, $LiBF_4$, $LiAsF_6$, $LiSbF_6$, $LiClO_4$, $LiAlCl_4$, $LiGaCl_4$, $LiNO_3$, $LiC(SO_2CF_3)_3$, $LiN(SO_2CF_3)_2$, LiSCN, $LiO_3SCF_2CF_3$, $LiC_6F_5SO_3$, $LiO_2CCF_3$, $LiSO_3F$, $LiB(C_6H_5)_4$, $LiCF_3SO_3$ or a combination thereof.

The additive is, for example, monomaleimide, polymaleimide, bismaleimide, poly-bismaleimide, copolymer of bismaleimide and monomaleimide, vinylene carbonate (VC) or a mixture thereof. The monomaleimide is, for example, selected from a group consisting of N-phenylmaleimide, N-(o-methylphenyl)-maleimide, N-(m-methylphenyl)-maleimide, N-(p-methylphenyl)-maleimide, N-cyclohexylmaleimide, maleimidophenol, maleimidobenzocyclobutene, phosphorus-containing maleimide, phosphoric acid group maleimide, oxasilylmaleimide, N-(tetrahydropyranyl-oxy-phenyl)maleimide and 2,6-ditolylmaleimide.

The packaging structure 112 encapsulates the anode 102, the cathode 104 and the electrolyte solution 108. The material of the packaging structure 112 is, for example, aluminum foil.

In particular, the cathode 104 can be formed by adding the oligomer of the invention to the cathode material in the current battery manufacturing process, therefore, under the condition that the change of battery design, battery material and electrolyte solution is not required, the capacity, battery efficiency and charge-discharge cycle life of the lithium battery 100 under high temperature can be effectively maintained, and the lithium battery 100 can have higher safety.

The effect of the oligomer of the invention is described in the following paragraphs with experimental examples and comparative examples.

Experimental Example 1

The epoxy acrylate resin (having the structure represented by formula 1, and R1 is propylene) and barbituric acid (having a structure represented by formula 3, and R3 and R4 is —H) in a molar ratio of 1:1 was added to a reactor loaded with N-methylpyrrolidone (NMP) solvent, and the reaction was performed under 130° C., to form the oligomer.

Comparative Example 1

N-phenylmaleimide and barbituric acid (having a structure represented by formula 3, and R3 and R4 is —H) in a molar ratio of 1:1 was added to a reactor loaded with N-methylpyrrolidone (NMP) solvent, and the reaction was performed under 130° C., to form the oligomer.

Figure 2:
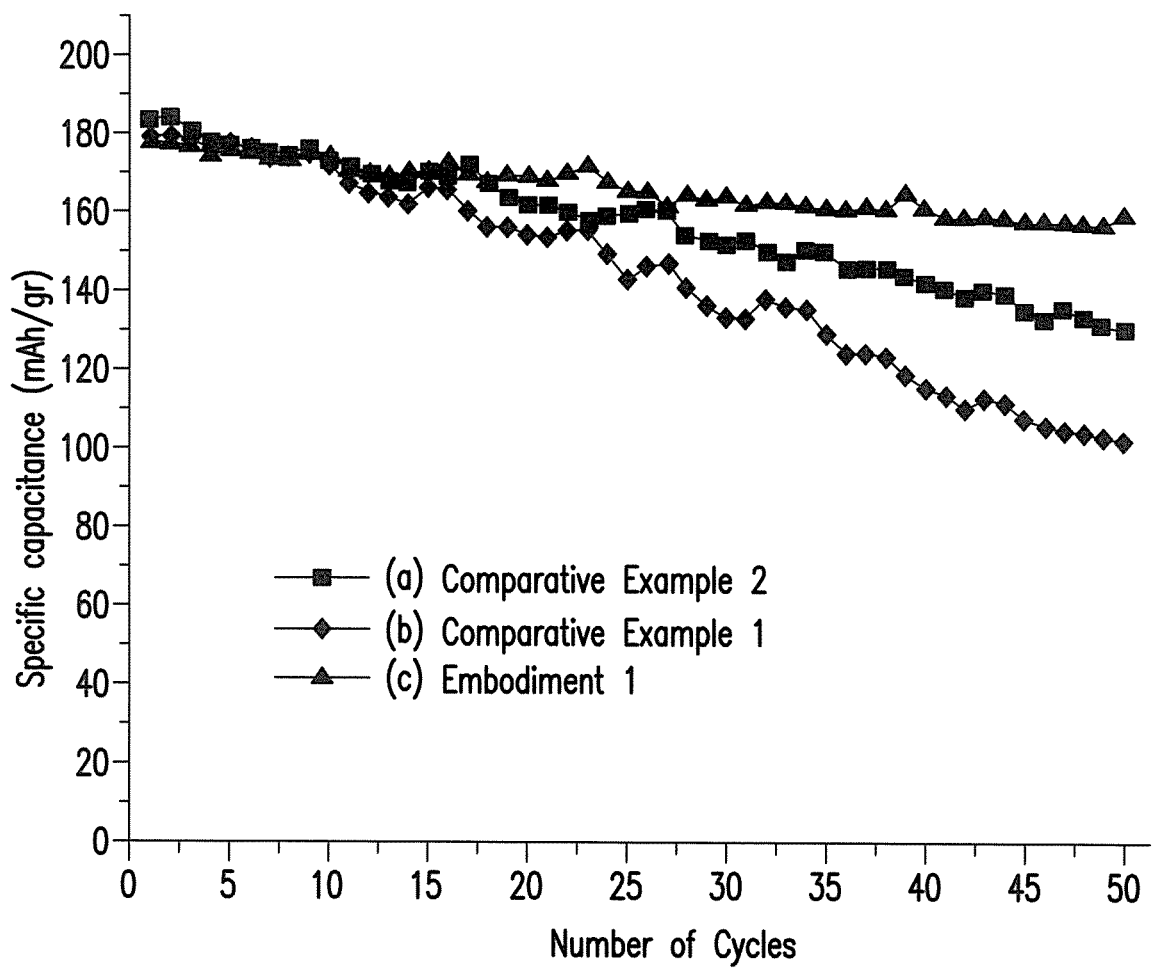
FIG. 2 is the relation diagram between the number of charge-discharge cycles and the discharge capacity of the lithium battery having the oligomer of experimental example 1, the lithium battery having the oligomer of comparative example 1 and the lithium battery without the oligomer in the room temperature.

The oligomer of the experimental example 1 and the comparative example 1 were applied to the same cathode material of the lithium battery respectively, and the cycle life test were performed on the lithium batteries. FIG. 2 is the relation diagram between the number of charge-discharge cycles and the discharge capacity of the lithium battery having the oligomer of experimental example 1, the lithium battery having the oligomer of comparative example 1 and the lithium battery without the oligomer (comparative example 2) in the room temperature. It can be clearly known from FIG. 2 that, when the lithium battery had the oligomer of the invention (experimental example 1), the battery life cycle is obviously increased (about 35% to 40%), it is illustrated that the oligomer of the invention can effectively increase the battery performance.

Figure 3A:
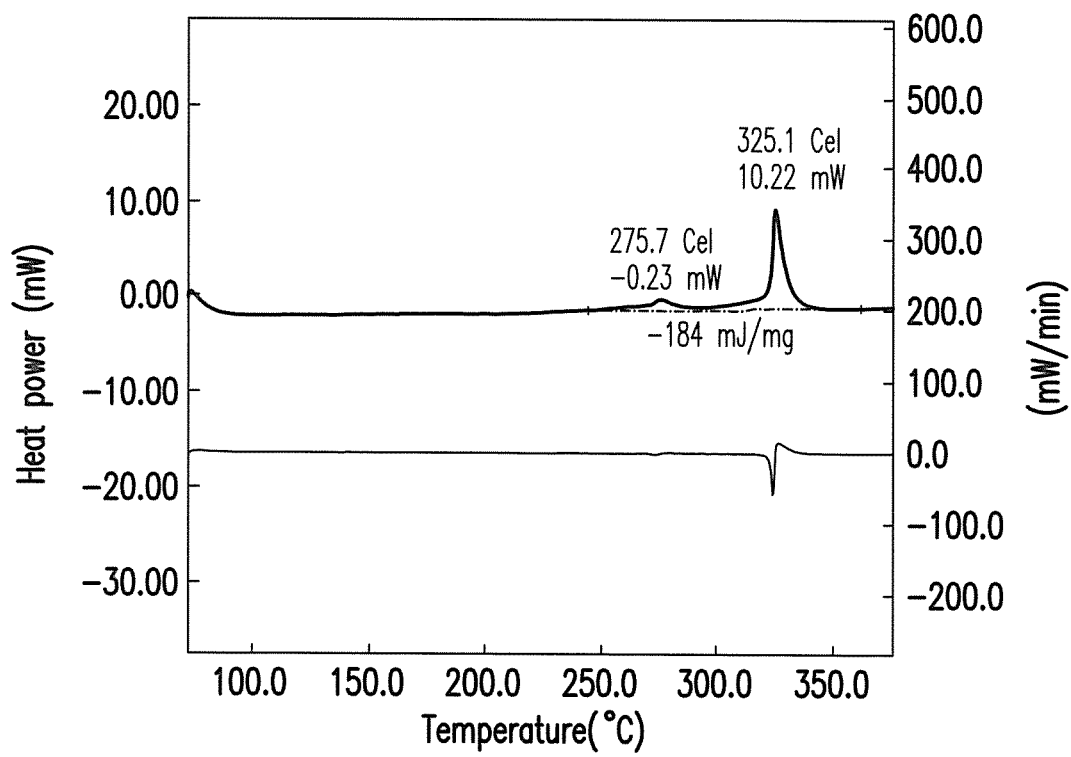
FIG. 3A is the result of the thermochemical heat release analysis performed on the oligomer of experimental example 1.
Figure 3B:
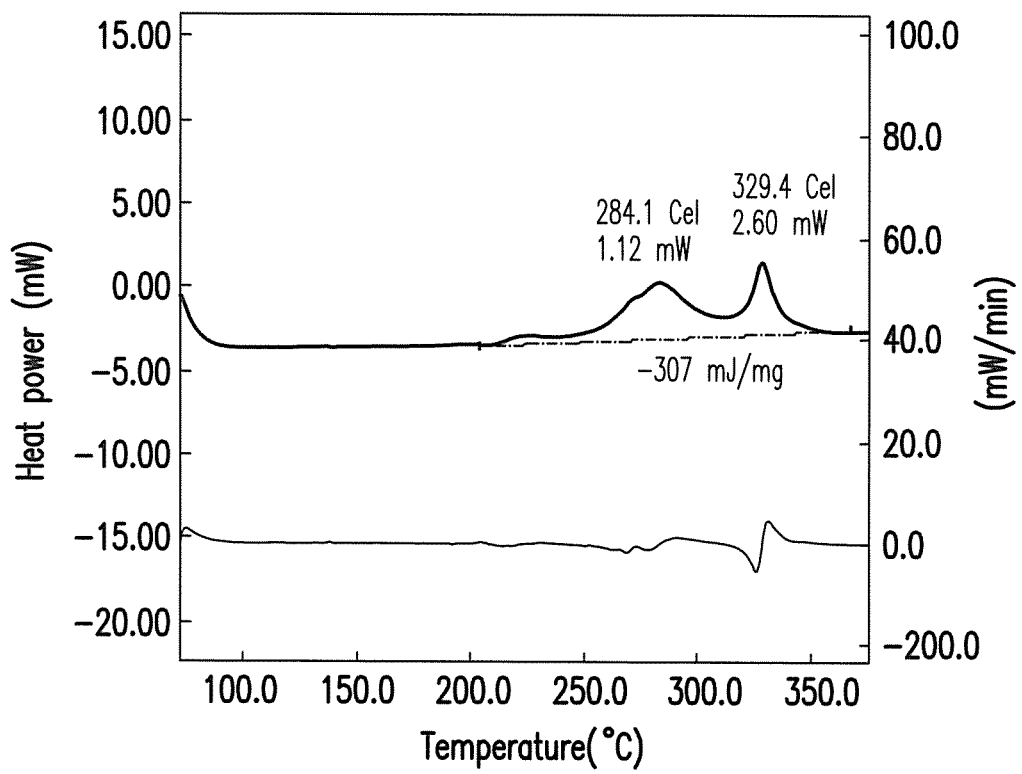
FIG. 3B is the result of the thermochemical heat release analysis performed on the oligomer of comparative example 1.

In addition, the thermochemical heat release analysis was performed on the electrodes having the oligomer of the experimental example 1 and the comparative example 1, the results were shown in FIG. 3A and FIG. 3B. It can be known from FIGS. 3A and 3B, compared to the electrode having the oligomer of the comparative example 1 (heat release is about 307 mJ/mg), the heat release of the electrode having the oligomer of the invention (experimental example 1) is about 184 mJ/mg, it is illustrated that the oligomer of the invention can effectively decrease the heat release of the lithium battery to achieve the safety goal, and, therefore, the life of the lithium battery can be effectively increased.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. An oligomer, obtained by reacting a reaction mixture consisting of epoxy acrylate resin, barbituric acid, and solvent.

2. The oligomer according to claim 1, wherein a molar ratio of the epoxy acrylate resin to the barbituric acid is between 1:1 and 4:1.

3. The oligomer according to claim 1, wherein the epoxy acrylate resin has at least one acrylic acid group.

4. The oligomer according to claim 3, wherein the epoxy acrylate resin has a structure represented by formula 1:

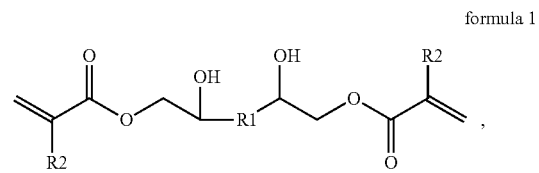

formula 1 wherein R1 is substituted or unsubstituted C1-C10 alkyl, or substituted or unsubstituted C6-C10 aryl; R2 is —H, —CH$_3$ or —CF$_3$.

5. The oligomer according to claim 3, wherein the epoxy acrylate resin has a structure represented by formula 2:

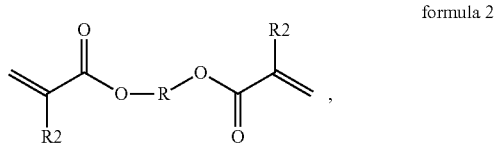

formula 2 wherein R is substituted or unsubstituted C1-C10 alkyl or an ether group; R2 is —H, —CH$_3$ or —CF$_3$.

6. The oligomer according to claim 5, wherein R is C1-C10 alkyl substituted by at least one acrylic acid group.

7. The oligomer according to claim 1, wherein the barbituric acid has a structure represented by formula 3:

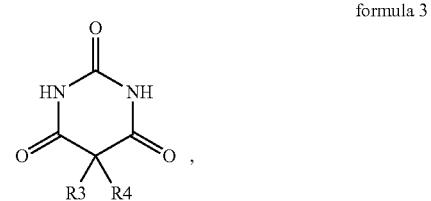

formula 3 wherein R3 and R4 are each independently —H, —CH₃, —C₂H₅, —C₆H₅, —CH(CH₃)₂, —CH₂CH(CH₃)₂, —CH₂CH₂CH(CH₃)₂ or

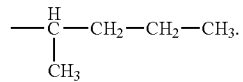

8. A lithium battery, comprising:
an anode;
a cathode, disposed separately from the anode, wherein the cathode comprises the oligomer according to claim 1;
a separator, disposed between the anode and the cathode, wherein the separator, the anode and the cathode define an accommodation area;
an electrolyte solution, disposed in the accommodation area; and
a packaging structure, encapsulating the anode, the cathode and the electrolyte solution.

9. The lithium battery according to claim 8, wherein the electrolyte solution comprises an organic solvent, lithium salt and an additive.

10. The lithium battery according to claim 9, wherein the additive comprises monomaleimide, polymaleimide, bismaleimide, poly-bismaleimide, copolymer of bismaleimide and monomaleimide, vinylene carbonate or a mixture thereof.

* * * * *